(12) United States Patent
Berlin et al.

(10) Patent No.: US 8,257,950 B2
(45) Date of Patent: Sep. 4, 2012

(54) BISULFITE CONVERSION OF DNA

(75) Inventors: Kurt Berlin, Stahnsdorf (DE); Matthias Ballhause, Berlin (DE); Karen Cardon, Albuquerque, NM (US)

(73) Assignee: Epigenomics AG, Berlin (DE)

( * ) Notice: Subject to any disclaimer, the term of this patent is extended or adjusted under 35 U.S.C. 154(b) by 0 days.

(21) Appl. No.: 13/159,323

(22) Filed: Jun. 13, 2011

(65) Prior Publication Data

US 2011/0250601 A1 Oct. 13, 2011

Related U.S. Application Data

(60) Division of application No. 12/410,389, filed on Mar. 24, 2009, now Pat. No. 7,968,295, which is a continuation of application No. 10/964,167, filed on Oct. 12, 2004, now abandoned, which is a continuation-in-part of application No. 10/311,661, filed as application No. PCT/DE01/02274 on Jun. 19, 2001, now Pat. No. 7,118,868.

(51) Int. Cl.
  *C12P 19/34* (2006.01)
  *C12Q 1/68* (2006.01)
(52) U.S. Cl. .................. 435/91.1; 435/6.1; 435/91.2
(58) Field of Classification Search ............ None
  See application file for complete search history.

(56) References Cited

U.S. PATENT DOCUMENTS

| 6,214,556 | B1 | 4/2001 | Olek et al. |
| 7,118,868 | B2 | 10/2006 | Berlin |
| 7,262,013 | B2 | 8/2007 | Boyd et al. |
| 2004/0033490 | A1 | 2/2004 | Laird et al. |
| 2004/0248120 | A1 | 12/2004 | Guetig |

FOREIGN PATENT DOCUMENTS

| WO | WO 01/98528 A2 | 12/2001 |
| WO | WO 02/38811 A2 | 5/2002 |
| WO | WO 02/081749 A2 | 10/2002 |
| WO | WO 03/038121 A2 | 5/2003 |
| WO | WO 03/064700 A2 | 8/2003 |
| WO | WO 2005/021803 A1 | 3/2005 |

OTHER PUBLICATIONS

Grunau et al., "Bisulfite Genomic Sequencing: Systematic Investigation of Critical Experimental Parameters," *Nucleic Acids Res.* (2001), 29(13):e65 (7 pages), Oxford University Press.

Paulin et al., "Urea Improves Efficiency of Bisulphite-Mediated Sequencing of 5'-methylcytosine in Genomic DNA," *Nucleic Acids Res.* (1998), 26(21):5009-5010, Oxford University Press.

*Primary Examiner* — James Martinell
(74) *Attorney, Agent, or Firm* — DLA Piper LLP (US)

(57) ABSTRACT

The present invention provides an improved method for the bisulfite conversion of DNA, and facilitates the analysis of cytosine methylation of genomic DNA. Novel combinations of denaturing solvents, new reaction conditions and new purification methods provide surprisingly efficacious methods for bisulfite conversion of DNA relative to prior art methods. The converted DNA may subsequently be analyzed by many different methods.

7 Claims, 4 Drawing Sheets

BISULFITE CONVERSION OF DNA

CROSS REFERENCE TO RELATED APPLICATIONS

This application is a divisional application of U.S. application Ser. No. 12/410,389 filed Mar. 24, 2009, now issued as U.S. Pat. No. 7,968,295; which is a divisional application of U.S. application Ser. No. 10/964,167 filed Oct. 12, 2004, now abandoned; which claims the benefit under 35 USC §119(a) to Germany Patent Application No. 103 47 400.5, Germany Patent Application No. 103 47 399.8, Germany Patent Application No. 103 47 397.1 and Germany Patent Application No. 103 47 396.3, all filed Oct. 9, 2003; and to U.S. application Ser. No. 10/311,611, now issued as U.S. Pat. No. 7,118,868; which is a 35 USC §371 National Stage application of International Application No. PCT/DE01/02274 filed Jun. 19, 2001; which claims the benefit under 35 USC §119(a) to Germany Patent Application No. 100 29 915.6, filed Jun. 19, 2000. The disclosure of each of the prior applications is considered part of and is incorporated by reference in the disclosure of this application.

BACKGROUND OF THE INVENTION

1. Field of the Invention

The present invention relates to methods for the detection of cytosine methylation in DNA.

2. Background Information

5-Methylcytosine is the most frequent covalently modified base in the DNA of eukaryotic cells. For example, it plays a role in the regulation of transcription, in genetic imprinting and in tumorigenesis (for review see Millar et al.: Five not four: History and significance of the fifth base: in S. Beck and A. Olek, eds.: The Epigenome; Wiley-VCH Verlag Weinheim 2003, S. 3-20). The identification of 5-methylcytosine as a component of genetic information is thus of considerable interest. 5-Methylcytosine positions, however, cannot be identified by sequencing, because 5-methylcytosine has the same base-pairing behavior as cytosine. Additionally, in the case of a PCR amplification, the epigenetic information borne by 5-methylcytosines is completely lost.

The usual methods for methylation analysis operate essentially according to two different principles. Either methylation-specific restriction enzymes are utilized, or a selective chemical conversion of unmethylated cytosines to uracil is conducted (bisulfite treatment). The enzymatically or chemically pretreated DNA is then amplified and can be analyzed in different ways (for review see Fraga and Esteller: DNA Methylation: A Profile of Methods and Applications: Biotechniques 33:632-649, September 2002; and see also WO 02/072880 pp. 1 ff).

As the use of methylation-specific enzymes is restricted to certain sequences containing restriction sites recognized by said enzymes, for most applications a bisulfite treatment is conducted review see U.S. patent application Ser. No. 10/311, 661).

According to the invention described herein below, a "bisulfite reaction", "bisulfite treatment" or "bisulfite method" refers to a reaction for the conversion of cytosine bases in a nucleic acid to uracil bases in the presence of bisulfite ions, whereby 5-methyl-cytosine bases are not significantly converted. The bisulfite reaction contains a deamination step and a desulfonation step which can be conducted separately or simultaneously (further details are described, and a reaction scheme is shown in EP 1394172A1, incorporated by reference herein in its entirety). There are various documents addressing specific aspects of the bisulfite reaction, including Hayatsu et al., Biochemistry 9:2858-28659, 1970; Slae and Shapiro, J. Org. Chem. 43:4197-4200, 1978; Paulin et al., Nucl. Acids Res. 26:5009-5010, 1998; Raizis et al., Anal Biochem. 226:161-1666, 1995; and Wang et al. Nucleic Acids Res. 8:4777-4790, 1980, and these documents, summarized in EP 1394172A1 are also incorporated by reference herein in their entirety.

The bisulfite treatment is usually conducted in the following way: The genomic DNA is isolated, mechanically or enzymatically fragmented, denaturated by NaOH, converted several hours by a concentrated bisulfite solution and finally desulfonated and desalted (e.g.: Frommer et al.: A genomic sequencing protocol that yields a positive display of 5-methylcytosine residues in individual DNA strands. Proc Natl Acad Sci USA. 89:1827-31, 1992, incorporated by reference herein in its entirety).

In recent times several technical improvements of the bisulfite methods were developed. The agarose bead method incorporates the DNA to be investigated in an agarose matrix, through which diffusion and renaturation of the DNA is prevented (bisulfite reacts only on single-stranded DNA) and all precipitation and purification steps are replaced by rapid dialysis (Olek A. et al. A modified and improved method for bisulphite based cytosine methylation analysis, Nucl. Acids Res. 24:5064-5066, 1996). In the patent application WO 01/98528 (=DE 100 29 915; =U.S. application Ser. No. 10/311,661), a bisulfite conversion is described in which the DNA sample is incubated with a bisulfite solution of a concentration range between 0.1 mol/l to 6 mol/l in presence of a denaturing reagent and/or solvent and at least one scavenger. In said patent application several suitable denaturing reagents and scavengers are described (document incorporated by reference herein in its entirety). In the patent application WO 03/038121 (=DE 101 54 317; =Ser. No. 10/416,624) a method is disclosed in which the DNA to be analysed is bound to a solid surface during the bisulfite treatment. Consequently, purification and washing steps are facilitated. Further improvement are described in the patent applications EP1394173A1 and EP1394172A1 (incorporated by reference herein in its entirety).

However, a basic problem of the bisulfite treatment consists of the fact that long reaction times are necessary in order to assure a complete conversion and to exclude false-positive results. Simultaneously, however, this leads to a degradation of the DNA due to the long reaction times. Higher reaction temperatures in fact lead to a higher conversion rate, but also to a more intense degradation of the DNA. The interactions between temperature, reaction time, rates of conversion and degradation were recently investigated systematically. In this way, it could be shown that the highest conversion rates were attained at temperatures of 55° C. (with reaction times between 4 and 18 hours) and at 95° C. (with a reaction time of one hour). A serious problem, however, is the degradation of the DNA during this procedure. At a reaction temperature of 55° C., 84-96% of DNA is decomposed. At 95° C. the degradation is in fact even higher (Grunau et al.: Bisulfite genomic sequencing: systematic investigation of critical experimental parameters. Nucleic Acids Res. 29:E65-5, 2001; incorporated by reference herein in its entirety). Thus, most authors use reaction temperatures of approximately 50° C. {see Frommer et al., loc. cit. 1992, p. 1827; Olek et al., loc. cit. 1996, p. 5065; Raizis et al: A bisulfite method of 5-methylcytosine mapping that minimizes template degradation, Anal Biochem 226:161-6, 162, 1995).

In addition to the high degradation rate of DNA, there is another problem in conventional bisulfite methods, which consists of the fact that a powerful purification method for converted DNA has not yet been described. Many authors use precipitations (see Grunau et al., loc. cit). A purification via DNA-binding surfaces has also been described (see Kawakami et al.: Hypermethylated APC DNA in plasma and prognosis of patients with esophageal adenocarcinoma, *Journal of the National Cancer Institute,* 92:1805-11, 2000). The yield of these purifications, however, is limited.

Due to the high losses of the conventional bisulfite treatment, it is problematic to use these methods for investigations in which the quantity of DNA to be analyzed is limited. A particularly interesting field of methylation analysis, however, lies in diagnosing cancer diseases or other disorders associated with a change in methylation status by means of analysis of DNA from bodily fluids, e.g. from blood or urine. However, DNA is present only in small concentrations in body fluids, so that the applicability of methylation analysis is limited by the low yield of conventional bisulfite treatment.

Accordingly, based on the particular importance of cytosine methylation analysis and based on the described disadvantages of conventional methodology, there is a great technical need for improved methods of bisulfite conversion.

BRIEF DESCRIPTION OF THE DRAWINGS

FIG. 3 shows the results of Example 4. The resulting gel from a electrophoresis after a PCR amplification is shown. Two different bisulfite-specific fragments, two nonspecific fragments and one genomic fragment were amplified each time. The uppermost panel shows the zero value (reaction time=0 hours). The second panel from the top shows the reaction with one thermospike and for one hour of total reaction time. The third panel from the top corresponds to the reaction with two thermospikes and two hours of total reaction time. The lowermost panel shows a reaction with 5 three thermospikes and three hours of reaction time. A large part of the DNA is converted even after one hour with the method according to the invention (second panel from the top). At the latest after three hours, genomic DNA can no longer be detected (lowermost panel).

SUMMARY OF THE INVENTION

According to the present invention, addition of certain denaturing solvents increases the conversion rate of the bisulfite reaction in an unexpected, surprising way. Simultaneously, the necessary reaction time and consequently the degradation rate are reduced. According to the present invention, the denaturing solvents disclosed herein provide unexpectedly strong and advantageous effects. Besides the clearly improved conversion rate and the reduced degradation rate the use of said solvent leads to another important advantage; namely lower concentration of bisulfite are used, whereas prior art bisulfite treatments are performed in the presence of high concentrations of bisulfite (Fraga and Esteller recommend a final concentration of 5 mol/l; supra, p. 642, left column, second paragraph). Such a high concentration of salt causes a high degradation and leads to problems within the subsequent purification and amplification.

A further advantage of the use of n-alkylenglycol compounds as a denaturing agent according to the present invention compared to the already known denaturing solvents is their higher water solubility. As a consequence, the reaction compounds, including the scavengers, are applicable in a broader concentration range. By combining the new solvents with optimized reaction conditions and new purification methods the efficacy of the conversion are further improved, and a sensitive DNA methylation analysis of tissue or bodily fluids is disclosed and provided.

In particular embodiments the present invention provides a method for bisulfite conversion of DNA, comprising reacting genomic DNA with a bisulfite reagent, wherein said reaction is carried out in the presence of a compound selected from the group consisting of dioxane, one of its derivatives, and a similar aliphatic cyclic ether. Preferably, the concentration of said compounds amounts to about 10-35%, or about 20-30%.

Additional embodiments provide a method for bisulfite conversion of DNA, comprising reacting genomic DNA with a bisulfite reagent, wherein said reaction is carried out in the presence of a compound with the following formula:

where
n=1-35000
m=1-3
$R_1$=H, Me, Et, Pr, Bu
$R_2$=H, Me, Et, Pr, Bu

Preferably, the compound comprises an n-alkylene glycol, a dialkyl ether, or diethylene glycol dimethyl ether (DME). Preferably, said compound is present in a concentration of about 1-35%, or about 5-25%.

Yet additional embodiments provide a method for bisulfite conversion of DNA, comprising reacting isolated genomic DNA with a bisulfite reagent, wherein the reaction is conducted at a temperature in the range of 0-80° C., and wherein the reaction temperature is briefly increased to a range of about 85-100° C. during the course of the conversion. Preferably, the number of temperature increases of brief duration amounts to 2 to 5. Preferably, during the temperature increases of brief duration, the reaction temperature increases to about 85 to 100° C. Preferably, the temperature increases of brief duration increase the reaction temperature to about 90 to 98° C. Preferably, the converted DNA is purified via magnetic particles.

Further embodiments provide a method for the bisulfite conversion of DNA, comprising reacting DNA with a bisulfite reagent, and purifying the converted DNA by means of ultrafiltration.

Preferably, in the embodiments of the present invention, bisulfite-converted DNA is analyzed, at least in part, by using at least one method selected from the group consisting of: MSP, HeavyMethyl, MsSNuPE and MethylLight. Preferably, DNA of tissue samples or bodily fluids is investigated.

Further embodiments provide a method for at least one of diagnosis and prognosis of an adverse event for patients or individuals, comprising use of the above described methods, wherein the adverse event is at least one event selected from the category group consisting of: undesired drug interactions; cancer diseases; CNS malfunctions, damage or disease; symptoms of aggression or behavioral disturbances; clinical, psychological and social consequences of brain damage; psychotic disturbances and personality disorders; dementia and/or associated syndromes; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, of the muscles, of the connective tissue or of the bones; endocrine and metabolic malfunction, damage or disease; headaches or sexual malfunction.

Additional embodiments provide a method for distinguishing cell types or tissues, or for investigating cell differentiation, comprising use of at least one of the above-described methods.

Further embodiments provide a kit, comprising: a reagent containing bisulfite; denaturing reagents or solvents, a radical scavenger, and primers for the production of amplificates. Preferably, the kit further comprises at least one of an ultra-filtration tube, and instructions for conducting an assay.

DETAILED DESCRIPTION OF THE INVENTION

One embodiment of the present invention provides a method for a bisulfite conversion of DNA, wherein DNA is reacted with a bisulfite reagent, characterized in that said reaction is carried out in the presence of a compound selected from the group consisting of dioxane, one of its derivatives, and a similar aliphatic cyclic ether.

Another embodiment of the present invention provides a method for a bisulfite conversion of DNA, wherein DNA is reacted with a bisulfite reagent, characterized in that said reaction is carried out in the presence of a compound of the following formula:

where
n=1-35000
m=1-3
$R_1$=H, Me, Et, Pr, Bu
$R_2$=H, Me, Et, Pr, Bu

Preferred are thus n-alkylene glycol compounds, particularly their dialkyl ethers, and especially diethylene glycol dimethyl ether (DME).

For both embodiments, the DNA to be investigated may originate from different sources depending on the diagnostic or scientific objective. For diagnostic investigations, tissue samples are preferably used as the initial material, but bodily fluids, particularly serum or plasma, can also be used. It is also possible to use DNA from sputum, stool, urine, or cerebrospinal fluid. Preferably, 5 the DNA is isolated from biological specimens. The DNA is extracted according to standard methods, from blood, e.g., with the use of the Qiagen Ultra-Sens™ DNA extraction kit. Other methods for purifying DNA are known to the person skilled in the art.

Subsequently, the isolated DNA may be fragmented, e.g., by reaction with restriction enzymes. The reaction conditions and the enzymes employed are known to the person skilled in the art and are taken, e.g., from the protocols supplied by the manufacturers.

The bisulfite conversion may be produced according to the known, protocols indicated above. The reaction may take place both in solution as well as also on DNA bound to a solid phase. Preferably sodium disulfite (=sodium bisulfite/sodium metabisulfite) is used, since it is more soluble in water than sodium sulfite. The disulfite salt disproportionates in aqueous solution to the hydrogen sulfite anions necessary for the cytosine conversion. When bisulfite concentration is discussed below, this refers to the concentration of hydrogen sulfite and sulfite anions in the reaction solution. For the method according to the invention, concentration ranges of 0.1 to 6 mol/l are possible (see above). Particularly preferred is a concentration range of 1 to 6 mol/l, and most particularly preferred, 2-4 mol/l. However, when dioxane is used, the maximal concentration of bisulfite that can be used is smaller (see below). In selecting the bisulfite concentration, one must consider that a high concentration of bisulfite leads to a high conversion, but also leads to a high decomposition rate due to the lower pH.

Dioxane can be utilized in different concentrations. Preferably, the dioxane concentration amounts to 10 to 35% (vol/vol), particularly preferred is 20 to 30%, and most particularly preferred is 22 to 28%, especially 25%. A dioxane concentration higher than 35% can be problematic, because this results in a formation of two phases within the reaction solution. In the particularly preferred embodiments with a dioxane concentration of 22-28%, the final preferred bisulfite concentration amounts to 3.3 to 3.6 mol/l, and in the most particularly preferred embodiment with a dioxane concentration of 25%, it amounts to 3.5 mol/l (see Examples herein).

The n-alkylene glycol compounds according to the invention can be utilized in a different concentration range. DME is preferably used in concentrations between 1-35% (vol/vol). There is preferably between 5 and 25%, and most preferably 10% DME.

The preferred scavengers utilized according to the invention are chromane derivatives, e.g., 6-hydroxy-2,5,7,8-tetramethylchromane 2-carboxylic acid (also known as: Trolox-C™). Further scavengers are listed in the patent application WO 01/98528 (=DE 100 29 915; =U.S. application Ser. No. 10/311,661; incorporated herein by reference in its entirety).

The bisulfite conversion can be conducted in a wide temperature range from 0 to 95° C. (see above). However, as at higher temperatures the rates of both the conversion and decomposition of the DNA increase, in a preferred embodiment the reaction temperature lies between 30-70° C. Particularly preferred is a range between 45-60° C.; most particularly preferred between 50-55° C. The optimal reaction time of the bisulfite treatment depends on the reaction temperature. The reaction time normally amounts to between 1 and 18 hours (see: Grunau et al. 2001, loc. cit.). The reaction time is ordinarily 4-6 hours for a reaction temperature of 50° C.

In a particularly preferred embodiment of the method according to the invention, the bisulfite conversion is conducted at mild reaction temperatures, wherein the reaction temperature is then clearly increased for a short time at least once during the course of the conversion. In this way, the effectiveness of the bisulfite conversion can be surprisingly clearly be increased. The temperature increases of short duration are named "thermospikes" below. The "standard" reaction temperature outside the thermospikes is denoted as the basic reaction temperature. The basic reaction temperature amounts to between 0 and 80° C., preferably between 30-70° C., most preferably 45°-55° C., as described above. The reaction temperature during a thermospike is increased to over 85° C. by at least one thermospike. The optimal number of thermospikes is a function of the basic reaction temperature. The higher the optimal number of thermospikes is, the lower is the basic reaction temperature. At least one thermospike is necessary in each case. And, on the other hand, in principle, any number of thermospikes is conceivable, f course, it must be considered that with a large number of temperature increases, the decomposition rate of the DNA also increases, and an optimal conversion is no longer assured. The preferred number of thermospikes is thus between 1 and 10 thermospikes each time, depending on the basic reaction temperature. A number of two to 5 thermospikes is thus particularly preferred. The thermospikes increase the reaction temperature preferably to 85 to 100° C., particularly preferably to 90-98° C., and most preferably to 94° C.-96° C.

The duration in time of the thermospikes also depends on the volume of the reaction batch. It must be assured that the temperature is increased uniformly throughout the total reaction solution. For a 20 ul reaction batch when using a thermocycler a duration between 15 seconds and 1.5 minutes, especially a duration between 20 and 50 seconds is preferred. In a particular preferred embodiment the duration is 30 seconds. Operating on a volume of 100 ul the preferred range lies between 30 seconds and 5 minutes, especially between 1 and 3 minutes. Particularly preferred are 1.5 minutes. For a volume of 600 ul, a duration of 1 to 6 minutes, is preferred, especially between 2 and 4 minutes. Particularly preferred is a duration of 3 minutes. A person skilled in the art will easily be able to determine suitable durations of thermospikes in relation to a variety of reaction volumes.

The above-described use of thermospikes leads to a significantly better conversion rates in the bisulfite conversion reaction, even when the above-described denaturing solvents are not utilized. According to the invention, a method for bisulfite conversion of DNA is hereby characterized in that the basic reaction temperature amounts to 0° C. to 80° C. and that the reaction temperature is increased for a short time to over 85° C. at least once in the course of the conversion. The initial material can be processed as described above.

The preferred temperature ranges, the number of thermospikes, and their duration correspond to the above-listed ranges. Accordingly, the basic reaction temperature amounts to between 0 and 80° C., preferably between 30-70° C., most preferably to 45°-55° C. The reaction temperature is increased to over 85° C. by at least one thermospike. The preferred number of thermospikes is between 1 and 10 thermospikes depending on the basic reaction temperature. Two to five thermospikes are particularly preferred. During the thermospikes the reaction temperature increases preferably to 85 to 100° C., particularly preferably to 90-98° C., and most preferably to 94° C.-96° C.

The duration in time of the temperature increases also depends on the volume of the reaction batch (see above).

After the bisulfite conversion is completed, the DNA is desulfonated and purified. Different methods are known for this purpose (e.g., see: DE 101 54 317 A1=U.S. Ser. No. 10/416,624; Grunau et al. 2001, loc. cit.). Normally, the reaction solution is first treated with sodium hydroxide. Subsequently, a neutralization and alcohol precipitation of the DNA are carried out. In a preferred embodiment of the above-described embodiments according to the invention, the purification is performed by means of a gel filtration, e.g., with Sephadex-G25 columns. The bisulfite salt can be removed very effectively in this way, without the need for further washing steps. In a second preferred embodiment, the purification is conducted via DNA-binding surfaces, e.g., via the Wizard DNA purification resin of Promega (see: Kawakami et al., loc. cit.). A third preferred embodiment utilizes magnetic particles for purification, e.g., with the help of the Magna-Pure process. These purification methods lead to particularly good results in combination with the n-alkylene glycol compounds according to the invention, particularly with DME. The purification is conducted according to the manufacturer's instructions. It is known to the person skilled in the art that an even further increased yield may be attainable by variation of the manufacturer's instructions by using standard experiments. Correspondingly, optimized protocols are also part of this invention. Further technical instructions for purifying nucleic acids via gel filtration, DNA-binding surfaces and magnetic particles are known to the person skilled in the art and are provided, e.g., from the manufacturer's instructions. In a most particularly preferred embodiment, purification is conducted by means of an ultrafiltration. Such a procedure has several technical advantages and results in a surprisingly successful purification of the converted DNA. The recovery rate of the converted DNA is very high (>85%, see Example 6). This is true for both, high-molecular DNA as well as also for fragmented DNA, such as found, e.g., in body fluids. The conventional methods for isolating bisulfite-treated DNA, in contrast, only lead to a recovery rate of approximately 25%. Ultrafiltration also has other advantages. For instance, purification is very flexible with respect to the volume of the samples to be used. In addition, the bisulfite salts can be removed almost completely. Furthermore, a desulfonation can be performed on the filter membrane, which additionally results in a savings in time. Different commercially available ultrafiltration systems are known to the person 5 skilled in the art, which may be used for the method according to the invention. In a preferred embodiment, Microcon™ columns of Millipore are used. The purification can thus be carried out according to a modified manufacturer's protocol. For this purpose, the bisulfite reaction solution is mixed with water and loaded onto the ultrafiltration membrane. Subsequently the reaction solution is centrifuged for about 15 minutes and then washed with 1×TE buffer. The DNA remains on the membrane in this treatment. Next, desulfonation is performed. For this purpose, 0.2 mol/l NaOH is added and the DNA incubated for 10 min. Another centrifugation (10 min) is then conducted, followed by a washing step with 1×TE buffer. The DNA is subsequently eluted. For this purpose, the membrane is mixed with 50 ul of warm 1×TE buffer (50° C.) for 10 minutes. The membrane is turned over according to the manufacturer's instructions and a repeated centrifugation is conducted, by means of which the DNA is removed from the membrane. Now the eluate can be used directly for the intended detection reactions. It is known to the person skilled in the art that other procedures may be indicated with other ultrafiltration systems, and that a good yield can also be obtained by varying the above-indicated conditions. The corresponding embodiments are also part of this invention.

The above-described use of ultrafiltration also facilitates a clearly improved purification of bisulfite-converted DNA, when the above-described denaturing solvents are not utilized or when conversion is conducted without thermospikes.

Therefore, according to the invention, a method for the bisulfite conversion of DNA is hereby characterized in that the purification of the converted DNA takes place by means of ultrafiltration. The initial material can thus be processed up as described above. Thermospikes may also be utilized. The preferred temperature ranges, the number of thermospikes, and their duration correspond to the above-listed ranges (see above). Also, ultrafiltration is preferably conducted as described above. Accordingly, different ultrafiltration systems may be utilized. In a preferred embodiment, the Micro-con™ columns of Millipore are used. The purification is preferably conducted as described above according to a modified manufacturer's protocol. It is known to the person skilled in the art that other procedures can be indicated with other ultrafiltration systems, and that an even further improved yield can also be obtained by varying the above-indicated conditions, he corresponding embodiments are also part of this invention.

The DNA which has been converted and purified via the above-described different embodiments may now be analyzed in different ways. It is particularly preferred to amplify the DNA first by means of a polymerase chain reaction. Thus, a selective amplification of the originally methylated or unmethylated DNA can be assured via different methods, e.g., via the so-called "Heavy-Methyl" method (for review see: Cottrell et al.; A real-time PCR assay for DNA-methylation using methylation-specific blockers. *Nucleic Acids Res.,* 32:el 0, 2004. WO 02/072880) or the so-called "methylation-sensitive PCR" ("MSP"; see: Herman et al.: Methylation-specific PCR: a novel PCR assay for methylation status of CpG islands. *Proc Nati Acad Sci USA.* 93:9821-6, 1996). The amplificates obtained may be detected via conventional methods, e.g., via primer extension reactions ("MsSNuPE"; see, e.g.: DE 100 10 280=U.S. Ser. No. 10/220,090) or via hybridization to oligomer arrays (see e.g.: Adorjan et al., Tumour class prediction and discovery by microarray-based DNA methylation analysis. Nucleic Acids Res., 30:e21, 2002). In another particularly preferred embodiment, the amplificates are analyzed with the use of PCR Real Time variants (see: U.S. Pat. No. 6,331,393 "Methyl Light"). Preferred variants are therefore the "Taqman" and the "Lightcycler" methods.

The methods disclosed here are preferably used for the diagnosis and/or prognosis of adverse events for patients or individuals, whereby these adverse events belong to at least one of the following categories: undesired drug interactions; cancer diseases; CNS malfunctions, damage or disease; symptoms of aggression or behavioral disturbances; clinical, psychological and social consequences of brain damage; psychotic disturbances and personality disorders; dementia and/or associated syndromes; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, of the muscles, of the connective tissue or of the bones; endocrine and metabolic malfunction, damage or disease; headaches or sexual malfunction.

The new method also serves in a particularly preferred manner for distinguishing cell types, tissues or for investigating cell differentiation.

The new method also serves in a particularly preferred manner for analyzing the response of a patient to a drug treatment.

The subject of the present invention is also a kit, which contains a reagent containing bisulfite, denaturing reagents or solvents, as well as scavengers, primers for the production of the amplificates as well as, optionally, an ultrafiltration tube or instructions for conducting an assay.

EXAMPLES

The following non-limiting examples facilitate disclosure of aspects of the broader invention.

Example 1

Automation of the Bisulfite Reaction

The application of the method for detecting the methylation state of cytosines in the factor VIII gene of a genomic DNA sample, which is treated with a restriction endonuclease according to the instructions of the manufacturer, is described in the present example. The method is based on the use of an automatic pipetting system (MWG RoboSeq 4204) with four separate vertically movable adapters for exchangeable pipetting tips, so as to exclude cross contaminations. The pipetting system makes possible the pipetting of 100 ul [aliquots] with an error of less than +2 ul. The operating plate of the automatic pipetting system is equipped with six racks for pipetting tips and eight 2 pipetting positions, two of which can be cooled, a reagent rack that can be cooled, a stacking system for 10 microtiter plates, a pipette tip washing station and a device for separating the pipette tips from the adapter.

The automatic pipetting system is connected to a computer by means of a serial interface and is controlled by means of a software program, which permits the free programming of all pipetting steps necessary for the application of the method.

In the first step of the method, an aliquot of the DNA sample is pipetted by hand into one of the 96 freely selectable positions of a microtiter plate. The microtiter plate is then subsequently heated to 96° C. with the use of an Eppendorf MasterCycler for denaturing the pretreated DNA sample. The microtiter plate is then transferred to the automatic pipetting system. Aliquots of a denaturing agent (dioxane), a 3.3 M sodium hydrogen sulfite solution, and a solution of a scavenger in the denaturing agent used are pipetted one after the other in a program-controlled manner from the reagent rack into all positions that contain DNA. Then the microtiter plate is incubated in the Eppendorf Mastercycler, so that all unmethylated cytosine residues in the DNA sample are converted into a bisulfite adduct with the action of the sodium hydrogen sulfite.

After the bisulfite treatment, the microtiter plate is transferred from the thermocycler to the automatic pipetting system. A second microtiter plate of the same type is then positioned. First, a basic Tris-HCl buffer (pH 9.5) and then an aliquot of the bisulfite-treated DNA are transferred into the corresponding positions of the second microtiter plate in all chambers whose equivalent positions on the first microtiter plate contain a bisulfite-treated DNA sample. The bisulfite adducts of the unmethylated cytosine residues are converted to uracil residues in the basic solution.

Figure 1:
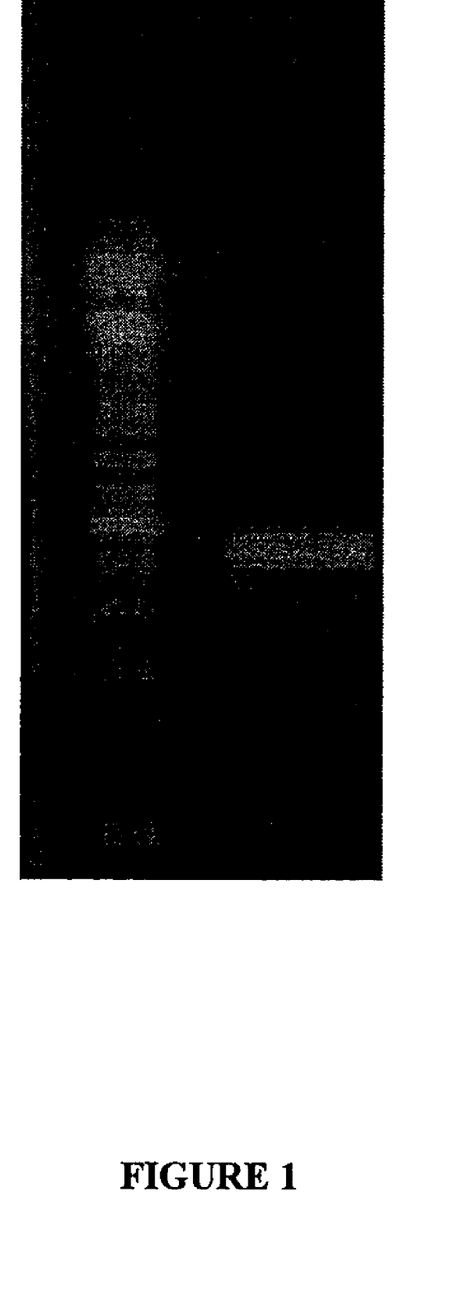
FIG. 1 shows the result of Example 1. The gel pattern of a PCR-amplified bisulfite-treated DNA strand is shown (left: molecular weight marker, right: PCR product).

The targeted amplification of one strand (the sense strand in the present example) of the bisulfite-treated DNA is conducted by a polymerase chain reaction (PCR). A pair of primers of type 1 (AGG GAG TTT TTT TTA GGG AAT AGA GGG A (SEQ. ID: 1) and TAA TCC CAA AAC CTC TCC ACT ACA ACA A (SEQ ID: 2) are used, which permit the specific amplification of a successfully bisulfite-treated DNA strand, but not a DNA strand, whose unmethylated cytosine residues were not converted to uracil residues or were incompletely converted. A third microtiter plate of the same type is positioned in the automatic pipetting system for the PCR reaction. In all chambers, whose equivalent positions on the first microtiter plate contain a bisulfite-treated DNA sample, an aliquot of a stock solution, which contains a PCR buffer, a DNA polymerase and a primer of type 1 is first automatically pipetted. Then, an aliquot of the diluted bisulfite-treated DNA is transferred automatically from each position of the second microtiter plate to the corresponding position of the third microtiter plate, before the latter is transferred to the cycler for conducting the PCR reaction. The PCR product is identified by agarose gel electrophoresis and subsequent staining with ethidium bromide (FIG. 1). FIG. 1 shows the gel image of a PCR-amplified bisulfite-treated DNA strand (left: molecular weight marker, right: PCR product).

Example 2

Optimized Bisulfite Conversion by Addition of Dioxane for the Detection of DNA in Plasma Samples The inventive optimized bisulfite method makes possible a sensitive methylation analysis of DNA obtained from body fluids. For example, 1 ml of human plasma was mixed with a specific quantity of human DNA. The DNA was isolated from the plasma samples via the Magna Pure method (Roche) according to the manufacturer's instructions. The 100 ul of eluate resulting from the purification were utilized completely in the following bisulfite reaction. The conversion according to a standard method (Frommer et al., loc. cit.) was conducted as a control. The procedure for the method according to the invention was as follows: The eluate was mixed with 354 ul of bisulfite solution (5.89 mol/l) and 146 ul of dioxane containing a radical scavenger (6-hydroxy-2,5,7,8-tetramethylchromane 2-carboxylic acid, 98.6 mg in 2.5 ml of dioxane). The reaction mixture was denatured for 3 min at 99° C. and subsequently incubated with the following temperature program for a total of 5 h: 30 min 50° C.; one thermospike (99.9° C.) for 3 min; 1.5 h 50° C.; one thermospike (99.9° C.) for 3 min; 3 h 50° C. The reaction mixtures of both the control as well as also of the method according to the invention were subsequently purified by ultrafiltration by means of a Millipore Microcon™ column. The purification was conducted essentially according to the manufacturer's instructions. For this purpose, the reaction mixture was mixed with 300 ul of water, loaded onto the ultrafiltration membrane, centrifuged for 15 min and subsequently washed with 1×TE buffer. The DNA remains on the membrane in this treatment. Then desulfonation is performed. For this purpose, 0.2 mo 1/1 NaOH was added and incubated for 10 min. A centrifugation (10 min) was then conducted, followed by a washing step with 1×TE buffer. After this, the DNA was eluted. For this purpose, the membrane was mixed for 10 minutes with 50 ul of warm 1×TE buffer (50° C.). The membrane was turned over according to the manufacturer's instructions. Subsequently a repeated centrifugation was conducted, with which the DNA was removed from the membrane. 10 ul of the eluate were utilized for the following Lightcycler™ Real Time PCR. A region of the human beta-actin gene was analysed (see Miyamoto: Nucleotide sequence of the human beta-actin promoter 5' flanking region; *Nucleic Acids Res.* 15:9095, 1987)). The following primer and probes were used: Forward primer: TGG TGA TGG AGO AGG TTT AGT AAG T (SEQ ID 3); reverse primer AAC CAA TAA AAC CTA CTC CTC CCT TAA (SEQ ID 4); donor probe: TTG TGA ATT TGT GTT TGT TAT TGT GTG TTG-flou (SEQ ID 5); acceptor probe: LC Red640-TGG TGG TTA TTT TTT TTA TTA GGT TGT GGT-Phos (SEQ ID 6). The amplification was conducted by means of a bisulfite-specific assay. The fluorescent signals were detected and calculated with the Lightcycle software. The amount of converted and isolated DNA could be quantified by a comparison with calibration curves. The optimized method produced a DNA concentration of 133.21 ng/100 ul, while the conventional method led to a concentration of 41.03 ng/100 ul. The method according to the invention thus made possible a yield that was three times higher than the conventional method.

Example 3

Figure 2:
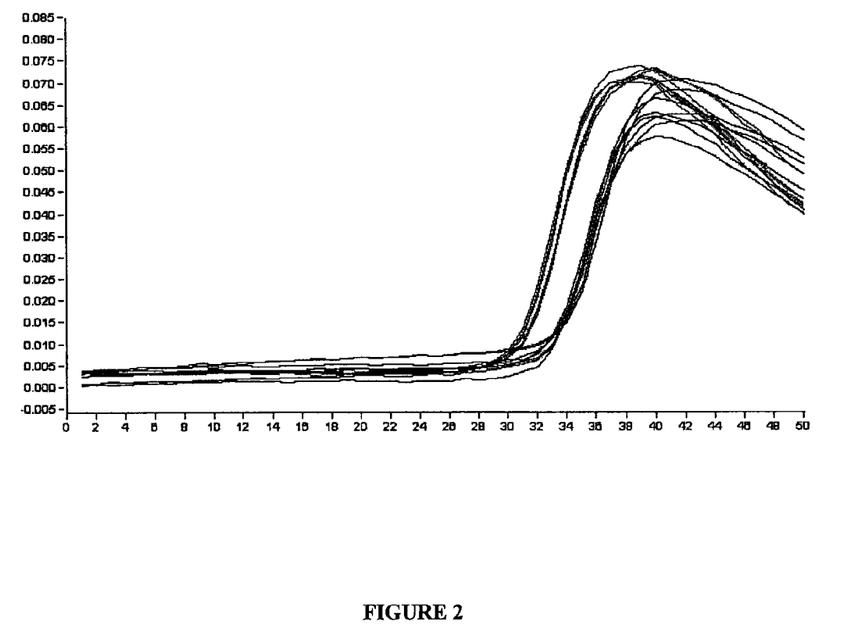
FIG. 2 shows the results of Example 3 (use of DME). DNA was isolated from plasma samples, treated with bisulfite and amplified by means of a Lightcycler PCR. The Y-axis shows the fluorescent signal measured in each cycle. The X-axis indicates the number of cycles. The curves of the method according to the invention are shown on the left and those of the conventional method are shown on the right. It is shown that the optimized method produces a significant fluorescent signal, even with a small number of cycles. The DNA yield is higher than with the conventional method.

Optimized Bisulfite Conversion by Addition of DME for the Detection of DNA in Plasma Samples It will be shown that the optimized bisulfite method makes possible a sensitive methylation analysis of DNA obtained from body fluids. For this purpose, 1 ml of human plasma was mixed with a specific quantity of human DNA. The DNA was isolated from the plasma samples via the Magna Pure method (Roche) according to the manufacturer's instructions. The 100 ul of eluate resulting from the purification were utilized completely in the following bisulfite reaction. Conversion according to a standard method (Frommer et al., loc. cit.) was conducted as a control. The procedure for the method according to the invention was as follows: The eluate was mixed with 354 ul of bisulfite solution (5.89 mol/l) and 46 ul of DME containing a radical scavenger (6-hydroxy-2,5,7,8-tetramethylchromane 2-carboxylic acid, 98.6 mg in 787 ul of DME). The reaction mixture was denatured for 3 min at 99° C. and subsequently incubated with the following temperature program for a total of 5 h: 30 min 50° C.; one thermospike (99.9° C.) for 3 min; 1.5 h 50° C.; one thermos-pike (99.9° C.) for 3 min; 3 h 50° C. The reaction mixtures of both the control as well as also of the method according to the invention were subsequently purified by ultrafiltration by means of a Millipore Microcon™ column. The purification was conducted essentially according to the manufacturer's instructions. For this purpose, the reaction mixture was mixed with 300 ul of water, loaded onto the ultrafiltration membrane, centrifuged for 15 min and subsequently washed with 1×TE buffer. The DNA remains on the membrane in this treatment. Then desulfonation is performed. For this purpose, 0.2 mol/l NaOH was added and incubated for 10 min. A centrifugation (10 min) was then conducted, followed by a washing step with 1×TE buffer. After this, the DNA was eluted. For this purpose, the membrane was mixed for 10 minutes with 50 ul of warm 1×TE buffer (50° C.). The membrane was turned over according to the manufacturer's instructions. Subsequently a repeated centrifugation was conducted, by means of which the DNA was removed from the membrane. 10 ul of the eluate were utilized for the following Lightcycler Real Time PCR. A region of the human beta-actin gene was analyzed by using the primers and probes described in Example 2. The amplification was conducted by means of a bisulfite-specific assay. The results calculated by the Lightcycler software are shown in FIG. 2. The curves on the left correspond to the optimized method, while the curves on the right correspond to the conventional method. It is shown that the optimized method produces a significant fluorescent signal, even with a small number of cycles. The DNA yield is thus higher than with the conventional method. The amount of converted DNA can be quantified by a comparison with calibration curves. The optimized method produced a DNA concentration of 133.27 ng/100 ul, while the conventional method led to a concentration of 41.03 ng/100 ul. The method according to the invention thus made possible a yield that was three times higher than the conventional method.

Example 4

Figure 3:
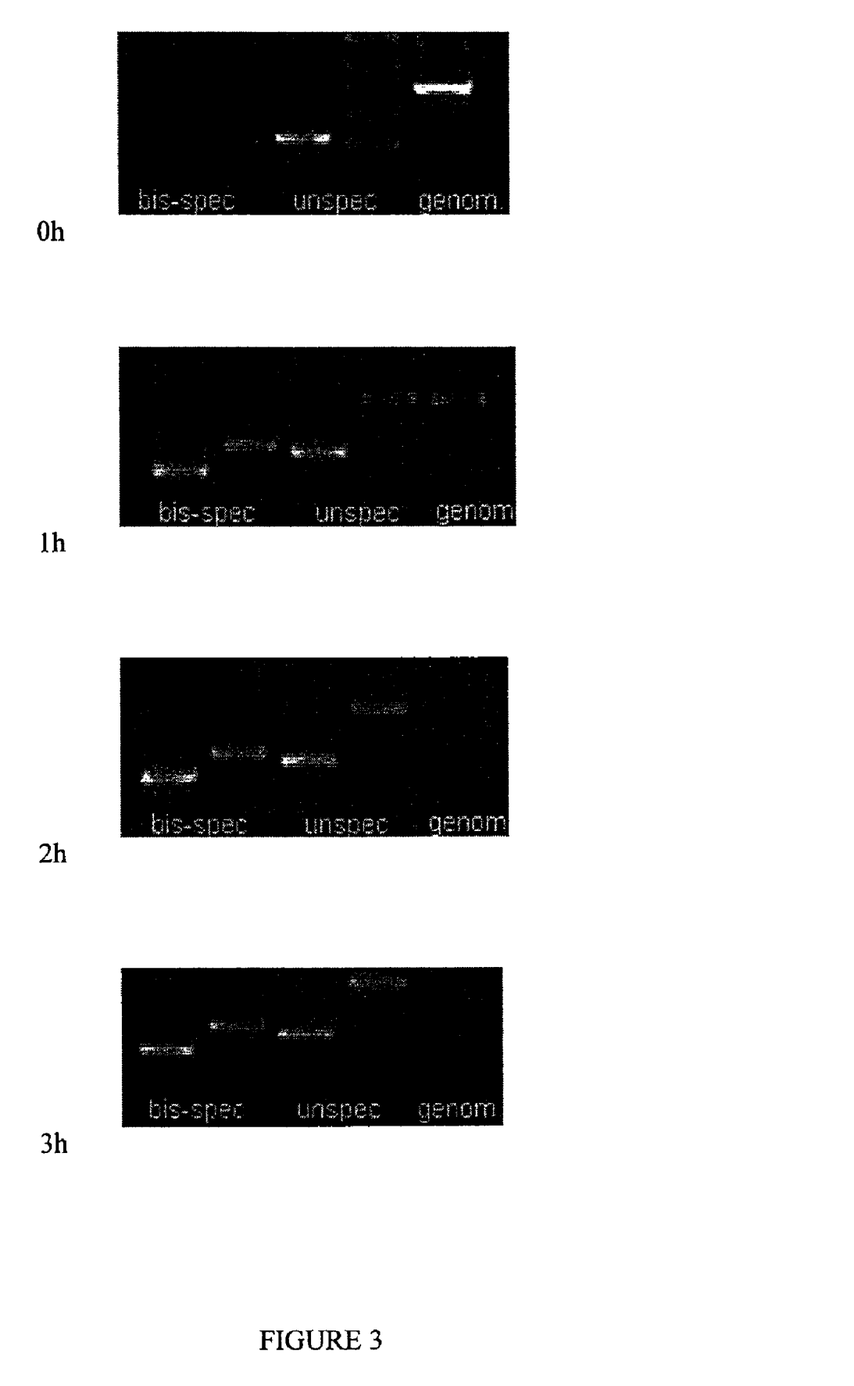

Bisulfite Conversion with Help of Thermospikes 2 ul of ddH$_2$0 were added to 1 ul of highly pure human DNA digested with MssI (Promega; 160 ng). The samples were denatured for 10 minutes at 96° C. Then roughly 10 ul of bisulfite solution (5.85 mol/l) and 7 ul of a radical scavenger/dioxane mixture (5 ul of dioxane plus 2 ul of scavenger) were added. After this, the first sample (0 h value) was removed and placed on ice. The reaction mixture was incubated for 30 seconds at 96° C. and subsequently for 59.5 minutes at 50° C. The second sample (1 h value) was removed and placed on ice. The third sample (2 h value) was incubated once more for 30 seconds at 96° C. and for 59.5 minutes at 50° C. Subsequently this sample was also placed on ice. The fourth sample (3 h value) was incubated once more for 30 seconds at 96° C. and for 59.5 minutes at 50° C., and subsequently also cooled. 30 ul of ddH$_2$0 were added to the samples. The reaction mixture was purified via G25 Sephadex columns. The eluate was mixed with 50 ul of 100 mmol/l Tris-HCl (pH 9.5) and desulfonated at 96° C. for 20 minutes. 2 ul of this solution were used for each PCR reaction. Two bisulfite-specific fragments, two nonspecific fragments and a genomic fragment were amplified each time in the PCR. The bisulfite-specific fragments are more intensely amplified, the further the bisulfite conversion has progressed. The nonspecific fragments are amplified independently of the bisulfite conversion and provide an indication of the degradation of the DNA. The genomic fragment is amplified only insofar as genomic DNA which is not converted with bisulfite is still present. The amplification of the genomic DNA is thus a measurement for an incomplete bisulfite conversion. The amplificates separated in agarose gels can be seen in FIG. 3. It is shown that in the method according to the invention, a large part of the DNA has been converted even after one hour. Genomic DNA can no longer be detected after three hours at the latest, i.e., the bisulfite conversion is complete. In conventional bisulfite treatment, corresponding values are produced at the earliest after 5 h (see below).

Example 5

Figure 4:
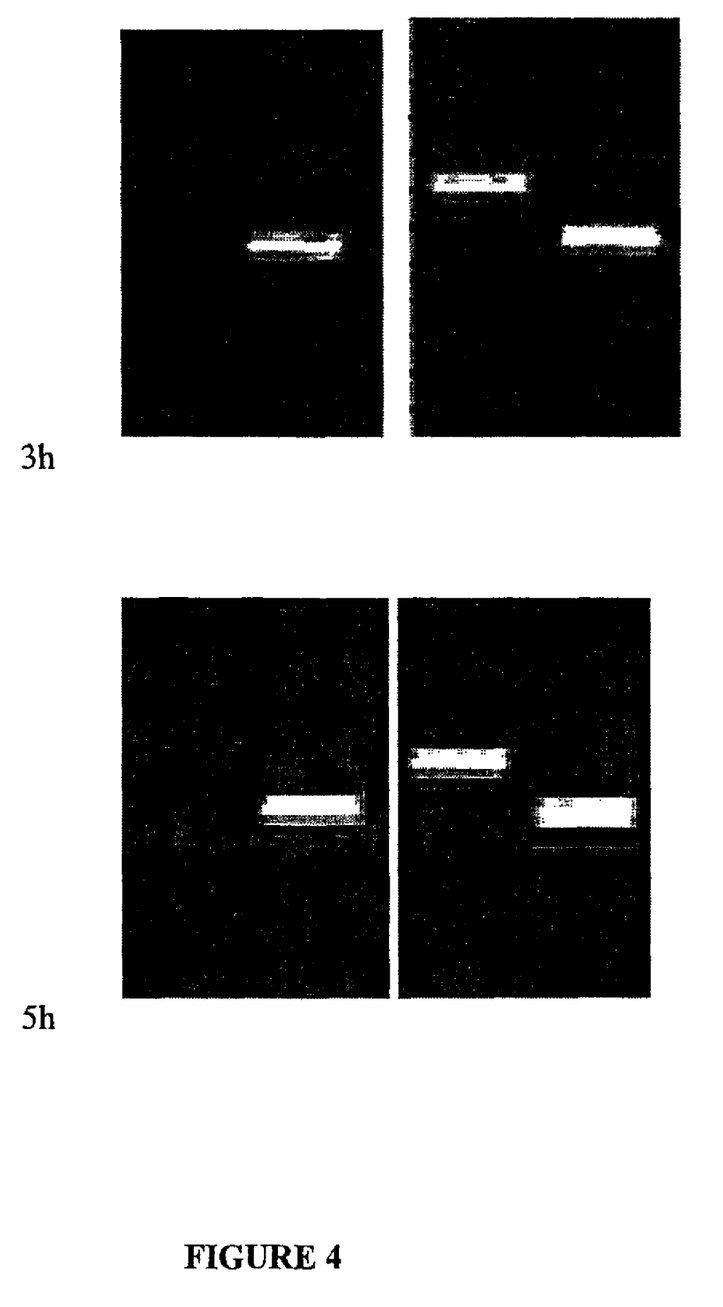
FIG. 4 shows the results of Example 5. The gel electrophoresis is shown after a PCR amplification. Two different bisulfite-specific amplificates were amplified. The panels on the left show conventional bisulfite treatment, while those on the right show the method according to the invention. A reaction time of 3 h is shown on the top and a reaction time of 5 h is shown on the bottom. A clearly more sensitive detection is possible with the method according to the invention (thermospikes). For example, therefore, the fragment shown in the left lane can be detected after 3 hours of reaction time, whereas the fragment from the conventional method still cannot be detected even after 5 hours of incubation.

Comparison of Bisulfite Treatment with Thermospikes to Bisulfite Treatment without Thermospikes Samples which were treated as in Example 4 were incubated with a reaction time of 3 or 5 h with two thermospikes. The controls were reacted without thermospikes. Purification and PCR were conducted as described above. Two bisulfite-specific fragments were amplified. One of the fragments was cytosine-rich. A relatively long reaction time was thus necessary in order to attain a complete conversion. The other fragment, in contrast, was cytosine-poor and was thus completely converted after a relatively short time. The results of the amplifications are shown in FIG. 4. The conventional bisulfite conversion can be seen in the figures on the left, while the optimized conversion with thermospikes can be seen in the figures on the right. The cytosine-rich fragment is plotted on the left each time, while the cytosine-poor fragment is plotted on the right. It is shown that the method according to the invention makes possible a clearly more sensitive detection. Therefore, the cytosine-rich fragment can be clearly detected even after 3 hours with a thermospike treatment, while it cannot be detected with the conventional method even after 5 hours of reaction time.

Example 6

DNA Recovery Rate in the Method According to the Invention

It will be shown that the method according to the invention makes possible a very effective bisulfite conversion and purification. For this purpose, different amounts of M13-DNA and human DNA were dissolved in 100 ul of water. The DNA solutions were mixed with 354 ul of bisulfite solution (5.89 mol/l) and 146 ul of dioxane containing a radical scavenger (6-hydroxy-2,5,7,8-tetramethylchromane 2-carboxylic acid, 98.6 mg in 2.5 ml of dioxane). The reaction mixture was denatured for 3 min at 99° C. and subsequently incubated with the following temperature program for a total of 5 h: 30 min 50° C.; one thermospike (99.9° C.) for 3 min; 1.5 h 50° C.; one thermospike (99.9° C.) for 3 min; 3 h 50° C. The reaction mixtures were subsequently purified by ultrafiltration by means of a Millipore Microcon™ column. The purification was conducted essentially according to the manufacturer's instructions. For this purpose, the reaction mixture was mixed with 300 µl of water, loaded onto the ultrafiltration membrane, centrifuged for 15 min and subsequently washed with 1×TE buffer. The DNA remains on the membrane in this treatment. Then desulfonation is performed. For this purpose, 0.2 mol/l NaOH was added and incubated for 10 min. A centrifugation (10 min) was then conducted, followed by a washing step with 1×TE buffer. After this, the DNA was eluted. For this purpose, the membrane was mixed for 10 minutes with 50 ul of warm 1×TE buffer (50° C.). The membrane was turned over according to the manufacturer's instructions. Subsequently, a repeated centrifugation was conducted, by means of which the DNA was removed from the membrane. The DNA concentrations were then determined fluorometrically (olive green). The data are shown in Table 1. The recovery rate of the DNA amounts to at least 75%. In the known methods for bisulfite conversion and purification of DNA, the recovery rates, in contrast, lie below 25%.

TABLE 1

| Utilized Amount of DNA in ng | M 13 DNA after Ultrafiltration | Human single-stranded DNA after Ultrafiltration |
| --- | --- | --- |
| 6000 | not determined | 108.5% |
| 4000 | not determined | 87.1% |
| 2000 | 86.91% | 84.8% |
| 1000 | 90.54% | 81.51% |
| 200 | 92.69% | 91.59% |
| 100 | 96.77% | 74.23% |

What is claimed is:

1. A method for bisulfite conversion of DNA, comprising reacting isolated genomic DNA with a bisulfite reagent, wherein the reaction is conducted at a temperature in the range of 0-80° C., and wherein the reaction temperature is increased at least once to a range of about 85-100° C. for a duration of between about 15 seconds and 6 minutes during the course of the conversion.

2. The method according to claim 1, wherein the temperature is increased from 2 to 5 times.

3. The method according to claim 1, wherein the reaction temperature is increased to about 90 to 98° C.

4. The method according to claim 1, wherein the converted DNA is purified via magnetic particles.

5. The method according to claim 1, wherein the DNA is from tissue samples or bodily fluids.

6. A method for at least one of diagnosis and prognosis of an adverse event for patients or individuals, comprising use of a method according to claim 1, wherein the adverse event is at least one event selected from the category group consisting of: undesired drug interactions; cancer diseases; CNS malfunctions, damage or disease; symptoms of aggression or behavioral disturbances; clinical, psychological and social consequences of brain damage; psychotic disturbances and personality disorders; dementia; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, of the muscles, of the connective tissue or of the bones; endocrine and metabolic malfunction, damage or disease; headaches or sexual malfunction.

7. A method for distinguishing cell types or tissues, or for investigating cell differentiation, comprising use of a method according to claim 1.

* * * * *

SEQUENCE LISTING

<160> NUMBER OF SEQ ID NOS: 6

<210> SEQ ID NO 1
<211> LENGTH: 28
<212> TYPE: DNA
<213> ORGANISM: artificial sequence
<220> FEATURE:
<223> OTHER INFORMATION: primer

<400> SEQUENCE: 1
agggagtttt ttttagggaa tagaggga                                    28

<210> SEQ ID NO 2
<211> LENGTH: 28
<212> TYPE: DNA
<213> ORGANISM: artificial sequence
<220> FEATURE:
<223> OTHER INFORMATION: primer

<400> SEQUENCE: 2
taatcccaaa acctctccac tacaacaa                                    28

<210> SEQ ID NO 3
<211> LENGTH: 25
<212> TYPE: DNA
<213> ORGANISM: artificial sequence
<220> FEATURE:
<223> OTHER INFORMATION: primer

<400> SEQUENCE: 3
tggtgatgga ggaggtttag taagt                                       25

<210> SEQ ID NO 4
<211> LENGTH: 27
<212> TYPE: DNA
<213> ORGANISM: artificial sequence
<220> FEATURE:
<223> OTHER INFORMATION: primer

<400> SEQUENCE: 4
aaccaataaa acctactcct cccttaa                                     27

<210> SEQ ID NO 5
<211> LENGTH: 30
<212> TYPE: DNA
<213> ORGANISM: artificial sequence
<220> FEATURE:
<223> OTHER INFORMATION: detection probe

<400> SEQUENCE: 5
ttgtgaattt gtgtttgtta ttgtgtgttg                                  30

<210> SEQ ID NO 6
<211> LENGTH: 30
<212> TYPE: DNA
<213> ORGANISM: artificial sequence
<220> FEATURE:
<223> OTHER INFORMATION: detection probe

<400> SEQUENCE: 6
tggtggttat tttttttatt aggttgtggt                                  30